United States Patent [19]
Kuzuya et al.

[11] Patent Number: 5,821,281
[45] Date of Patent: *Oct. 13, 1998

[54] ORGANIC POLYMER COMPOUND AND PRODUCTION THEREOF

[75] Inventors: Masayuki Kuzuya, Gifu Prefecture; Sumio Watanabe, Ibaraki Prefecture, both of Japan

[73] Assignee: Eisai Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 735,210

[22] Filed: Oct. 22, 1996

Related U.S. Application Data

[60] Continuation of Ser. No. 319,578, Oct. 7, 1994, abandoned, which is a division of Ser. No. 862,763, filed as PCT/JP91/01449, Oct. 23, 1991, abandoned.

[30] Foreign Application Priority Data

Oct. 24, 1990 [JP] Japan .................................. 2-284127

[51] Int. Cl.[6] ...................................................... C08F 2/56
[52] U.S. Cl. ........................... 522/175; 522/174; 522/182; 522/183; 424/78.31; 424/78.32; 424/78.35
[58] Field of Search .............................. 424/78.32, 78.35, 424/78.31; 522/174, 182, 183, 175

[56] References Cited

U.S. PATENT DOCUMENTS

| | | | |
|---|---|---|---|
| 4,001,172 | 1/1977 | Steinkamp et al. | 524/504 |
| 4,003,990 | 1/1977 | Jacquet et al. | 424/78.32 X |
| 4,225,693 | 9/1980 | McCormick | 576/761 |
| 4,430,265 | 2/1984 | Yamamura et al. | 532/322 |
| 4,772,463 | 9/1988 | Zappia et al. | 424/78 |
| 5,053,228 | 10/1991 | Mori et al. | 424/78.31 |
| 5,108,740 | 4/1992 | Greenwald et al. | 424/78.32 |

FOREIGN PATENT DOCUMENTS

| | | |
|---|---|---|
| 54-003389 | 1/1979 | Japan . |
| 54-120696 | 9/1979 | Japan . |
| 59-161414 | 9/1984 | Japan . |
| 62-129296 | 6/1987 | Japan . |
| 6460615 | 7/1989 | Japan . |
| 3083914 | 4/1991 | Japan . |

OTHER PUBLICATIONS

D. Bremmer, Chemistry in Britain, Jul. 1986, 633–638.
G J Price et al. (1990), Brit. Polym. J. 23, 63–66.
Merck Index, 9th Ed., 1976, p. 786.
Hawley's Condensed Chemical Dictionary, 11th Ed., Van Nostrand, New York, 1987, p. 424.
Aldrich Catalog, 1990–1991, pp. 890, 1081.
Aldrich Catalog Handbook of Fine Chemicals, 1996–1997, pp. 34, 936, 959, 1002.
M. Kuzuya et al. (1991) Macromol. 24, 4047–4053.
P. Kruus et al. (1985) J. Phys. Chem 89, 3379–3384.

*Primary Examiner*—Mark Nagumo
*Attorney, Agent, or Firm*—Wenderoth, Lind & Ponack, L.L.P.

[57] ABSTRACT

A homopolymer of acrylic acid or methacrylic acid derivatives having the general formula:

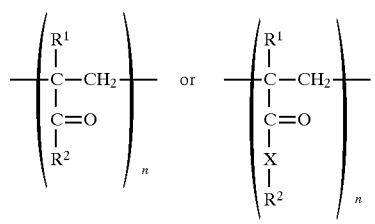

wherein $R^1$ represents a hydrogen atom or methyl group; $R^2$ is a residue of a compound having physiological activity; X is a residue of a compound having a hydroxyl group, amino group or carboxyl group at both ends in its chemical structure after bonding between such compound and acrylic or methacrylic acid, and between such compound and the physiologically active compound; and the homopolymer has a number-average molecular weight ranging from 20,000 to 200,000; and a process for the preparation thereof by a mechanochemical polymerization reaction; as well as a polymeric drug and prodrug comprising the homopolymer.

3 Claims, No Drawings

5,821,281

ORGANIC POLYMER COMPOUND AND PRODUCTION THEREOF

This is a continuation of application Ser. No. 08/319,578, filed Oct. 7, 1994, now abandoned which is a divisional of application Ser. No. 07/862,763, filed Jun. 23, 1992, now abandoned which is a national phase application of PCT/JP91/01449 filed Oct. 23, 1991.

FIELD OF THE INVENTION

The present invention relates to an acrylic or methacrylic polymer to which a chemical compound having physiological activity is chemically bonded. More particularly, the present invention relates to a polymeric drug comprising an acrylic or methacrylic polymer to which a chemical compound having physiological activity is bonded, wherein the polymeric drug releases a physiological active substance in vivo, and to a process for the preparation of said polymer by means of mechanochemical polymerization method.

PRIOR ARTS

In general, a polymeric substance has various kinds of properties and functions and is significantly different from a low molecular substance in its behavior in vivo.

Therefore, an attempt has been made to chemically bond a low molecular physiological active substance to a polymeric substance having no physiological activity in order to form a polymeric drug, so that behavior in vivo or interaction with cells may be controlled.

As a process for the preparation of a polymeric drug, there is known a process for bonding a low molecular physiological active substance to a polymeric substance such as dextrane, albumin and the like. However, this process has drawbacks in requiring a great deal of labor for purification of the reaction products, removal of reaction solvents, and the like. While there are known processes for obtaining polymeric drugs by polymerization of a monomer to which a low molecular physiological substance is bonded, there is no practical process, since the prior processes have several disadvantages that removal of residual solvent is required because the processes are carried out in a solvent, and molecular weight distribution of the polymeric drugs obtained is wide and it is moreover difficult to obtain the product in a yield of 100%.

On the other hand, study has been made wherein mechanochemical reactions, that is, chemical reactions caused by mechanical actions are effected with respect to polymeric substances or inorganic substances. For example, a mechanochemical polymerization reaction in a solid phase is most frequently carried out in the presence of a catalyst under mechanical forces such as grinding, rubbing and so forth.

It is known that a solid phase polymerization reaction of vinyl monomer such as acrylamide, etc. makes progress under an irradiation with high energy radiation such as γ-ray, or X-ray to effect polymerization. However, the radiation polymerization process has the defects that the polymerization rate is low and the physiological active substance used may be unfavorably decomposed.

SUMMARY OF INVENTION

As a result of concentrated study on the syntheses of a novel polymeric drug, the present inventors have found that the drawbacks of the above-mentioned prior arts for a polymeric drug can be overcome by using a mechanochemical reaction and that the mechanochemical reaction used is therefore novel per se, and established the present invention.

DETAILED DESCRIPTION OF INVENTION

Accordingly, the present invention relates to a polymeric drug obtained by polymerizing acrylic or methacrylic acid derivatives to which a low molecular physiological active substance is bonded by virtue of an ester linkage or amide linkage, and also to a process for the synthesis thereof by mechanochemical polymerization reaction.

The polymeric drug according to the present invention may be termed "prodrug", since it is hydrolyzed or decomposed by enzyme in vivo, to release a low molecular physiological active compound.

Accordingly, an object of the present invention is to provide a novel polymeric drug for use as a prodrug releasing a low molecular physiological active substance in vivo and a process for the preparation thereof by virtue of mechanochemical polymerization reaction.

In the present invention, the low molecular physiological active compound may be one having a molecular weight of 1,000 or less and a functional group such as a hydroxyl group or amino group which is able to react with a carboxyl group contained in an acrylic acid or methacrylic acid. Illustrative of the low molecular physiological active compounds are various kinds of drugs having remedial effects such as acetaminophen, theophylline, fluorouracil, amphotericin B, methyldopa, nicotinic acid amide, cephalexin, and the like.

When it is difficult to directly react acrylic acid or methacrylic acid with a low molecular physiological active substance, any appropriate spacer may be interposed between acrylic acid or methacrylic acid and a low molecular physiological active substance. The spacer may have a functional group at the ends of a carbon chain containing 1 to 10 carbon atoms such as hydroxyl group or amino group which is able to react with a carboxyl group contained in acrylic acid or methacrylic acid or a functional group contained in a low molecular physiological active substance.

In the present invention, the mechanochemical polymerization reaction means a polymerization reaction resulting from adding mechanical energy such as grinding, rubbing, high-speed vibration or compression etc. at a room temperature to an acrylic acid monomer or methacrylic acid monomer to which a low molecular physiological active compound is chemically bonded. Any various optional processes may be selected, depending upon the properties of the monomer used.

Accordingly, when the low molecular physiological active compound is bonded by ester linkage to an acrylic acid or methacrylic acid, the mechanochemical polymerization reaction progresses by only carrying out grinding or high-speed vibration in a metal container at a room temperature under atmosphere of nitrogen, thereby obtaining a polymeric drug to which the physiological active substance is chemically bonded. It may be conceived that the polymerization reaction in this case starts by transferring electrons onto a vinyl group of the monomer from the surface of metal to result in free radicals. The polymerization reaction may be supposed to progress by chain reaction, once the radicals are formed.

The significant characteristics of the process of the present invention is that while the molecular weight of the polymeric drug formed at the initial stage of the polymerization reaction is so high as to rapidly reach the maximum value, a lowering of molecular weight continues until it reaches the limiting molecular weight, when the polymer chain of the polymer formed is cut by grinding.

The time required for reaching the limiting molecular weight is not unconditionally critical, and depends upon the size and performance of the apparatus used, although it will be normally 20 minutes and over. The average molecular weight at the limiting molecular weight may be 3,000 or thereabout. The polymeric drug synthesized by the process of the present invention is a so-called homopolymer, and a random copolymer may be obtained by grinding it together with another solid monomer such, for example, as acrylamide. The physico-chemical properties of the resulting prodrug may be changed by the use of acrylamide, etc. Mechanochemical polymerization reaction does not proceed by the use of only a compound, wherein a cyclic low molecular compound having physiological activity is directly bonded to methacrylic acid, such as methacryloyl derivatives of 5-fluorouracil, for example, 1-methacryloyl-5-fluorouracil. In this case, the mechanochemical polymerization reaction can take place by introducing an acryloyl group or a methacryloyl group to form a monomer or by carrying out the operations including grinding under atmosphere of nitrogen together with a compound easily forming a mechanoradical such as polyacrylic acid, polymethylacrylate, polymethacrylic acid, polymethylmethacrylate, polyacrylamide and polymethacrylamide. The container used in this case may be a glass container or TEFLON container. According to the present invention, the mechanoradical formation resulted from the cleavage of polyacrylic acid, etc. by means of mechanical energy is the starting stage of polymerization reaction, followed by the same reaction process as above mentioned to form a polymer having the limiting molecular weight, and a polymeric drug having an average molecular weight of 30,000 or thereabout can be obtained. The polymeric drug synthesized by the process is a so-called block-copolymer.

The polymeric drug of the present invention is a homopolymer having the general formula:

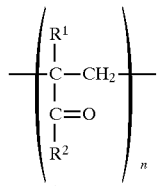
(I)

wherein $R^1$ represents a hydrogen atom or methyl group; $R^2$ represents a residue after bonding by ester linkage or amide linkage in the compound having a physiological activity, and containing a functional group capable of ester linkage or amide linkage with a carboxyl group in its chemical structural formula; and, in case of a random copolymer, $R^2$ represents a residue as defined above or a residue of the other monomer.

Alternatively, the polymeric drug is a block copolymer having the general formula:

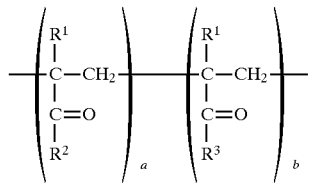
(II)

wherein $R^1$ and $R^2$ have the same meaning as defined above; $R^3$ represents a hydroxyl group, an alkoxyl group or amino group; a represents an integer ranging from 20 to 1,500: and b represents an integer ranging from 1 to 100, respectively.

Number-average molecular weight ranges from 20,000 to 200,000, providing that it varies depending upon polymerization time, physiological active substance bonded to main chain and so forth.

The symbol "a" in the general formula (II) ranges from about 150 to 1,500, when the molecular weight of $R^2$ is 100, and ranges from about 20 to 200 when it is 1000. Accordingly, "a" may have a value ranging from about 20 to 1,500.

And, the symbol "b" in the general formula (II) may have, in general, a value ranging from 1 to 100 depending upon the radical initiator such as polyacrylic acid, etc. Since it is difficult in a polymer to define precisely the values of "a" and "b", the values for "a" and "b" above shown are nothing but standards.

As stated above, a spacer may be interposed between acrylic acid or methacrylic acid and a low molecular physiological active substance. The polymeric drug in this case is represented by the general formula:

(III)

wherein $R^1$ represents a hydrogen atom or methyl group; $R^2$ represents a reside after bonding by ester linkage or amide linkage in the compound having a physiological activity, and containing a functional group in its chemical structural formula capable of ester linkage or amide linkage with a carboxyl group or amino group; X represents a residue of a compound having, at both ends thereof, the same or different two functional groups selected from the group consisting of a hydroxyl group, amino group and carboxyl group, after bonding by ester linkage or amide linkage between one of the functional groups and a carboxyl group contained in acrylic acid or methacrylic acid, and between the other functional group and the physiological active compound; and the number-average molecular weight of the polymeric drug ranges from 20,000 to 200,000.

Alternatively, the polymeric drug is represented by the general formula:

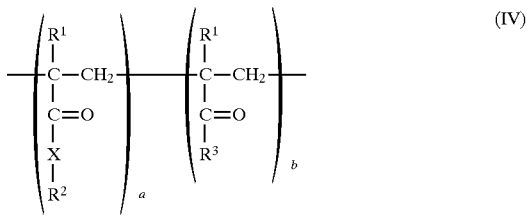
(IV)

wherein $R^1$ represents a hydrogen atom or methyl group; $R^2$ represents a residue after bonding by ester linkage or amide linkage in the compound having a physiological activity, and containing a functional group capable of ester linkage or amide linkage with a carboxyl group or amino group in its chemical structural formula; X represents a residue of a compound having, at both ends thereof, the same or different two functional groups selected from the group consisting of a hydroxyl group, amino group and carboxyl group, after bonding by ester linkage or amide linkage between one of the functional groups and a carboxyl group contained in acrylic acid or methacrylic acid, and between the other functional group and the physiological active compound; $R^3$ represents a hydroxyl group, methoxyl group or amino group; a represents an integer ranging from 20 to 1,500; and b represents an integer ranging from 1 to 100, respectively.

The polymeric drug of the present invention has a polydispersibility of 1.1 or less, and has the great advantage in that the molecular-weight distribution is very narrow.

It is known that the mechanism of a polymer in vivo is so dependent upon its molecular weight, and it provides a possibility of precise control of the polymeric drug in vivo that the polydispersibility of the polymeric drug obtained by the present invention is low and molecular-weight distribution is narrow.

Further, the polymerization reaction proceeds approximately 100% according to the mechanochemical reaction of the present invention, and hence, the present invention has the advantage of requiring no after-treatments such as purification, etc. due to no use of solvents.

In order to obtain the polymeric drug of the present invention, it is firstly required to obtain a monomer of acrylic acid or methacrylic acid derivatives by reacting a low molecular physiological active substance with acrylic acid or methacrylic acid. The above-mentioned monomer may be obtained in the manner as stated below, in case of using p-acetaminophenone, for example. That is, p-acetaminophenone is dissolved in an acetonitirile anhydride, and methacryloyl chloride is added drop by drop to the solution. The resulting reaction solution is stirred for 30 minutes at a room temperature, followed by the removal of a reaction solvent by distillation. The residue is dissolved in chloroform, and dried, followed by recrystallization from benzene to obtain p-methacryloyloxyacetanilide.

The monomer thus obtained is put into a grinding mill made of stainless steel and ground for 45 minutes under atmosphere of nitrogen to obtain the polymeric drug.

The present invention is explained more in detail by referring to the following Examples given by way of illustration, but not by way of limitation.

EXAMPLES

Example 1

To dried acetonitrile (60 ml) were added p-acetaminophenol (1 g; 6 mmols), followed by slowly adding dropwise methacryloyl chloride (0.73 g; 7.2 mmols). After the resultant reaction solution was stirred for 30 minutes at a room temperature, the reaction solvent was removed by distillation. The residue was dissolved in chloroform (30 ml), washed twice with water (10 ml) and dried, followed by the removal of chloroform by distillation, and then subjected to recrystallization from benzene.

The yield of the resulting p-methacryloylacetamide was 0.8 g.

The following are the data on crystalline form, melting point, elemental analysis, IR, $^1$H-NMR and UV-spectrum:

Colorless needle
Melting point: 120°–121° C.
Elemental analysis: $C_{12}H_{13}NO_3$ (219.24)

|  | C | H | N |
|---|---|---|---|
| Calculated | 65.74 | 5.98 | 6.39 |
| Found | 65.53 | 5.98 | 6.14 |

IR(KBr): 1730, 1660 cm$^{-1}$ (>C=O)
$^1$H-NMR(270 MHz, DMSO-d$_6$): δ; 2.00(S, 6H, —CH$_3$), 5.8–6.3 (d, 2H, >=CH$_2$), 7.0–7.7 (q, 4H, benzene ring), 10.0(S, 1H, >NH)
UV(ethanol): $\lambda_{max}$; 273 nm(ε=8000), MS:m/e 219(M$^+$)

The resulting monomer (100 mg) was put under atmosphere of nitrogen into the grinder provided with a stainless steel mill, and ground for 45 minutes to obtain a polymer.

When the polymer obtained was analyzed by means of $^1$H-NMR spectrum, the protons contained in the olefin constituting the monomer were completely absent and peaks of strength (broad) corresponding to alkyl site were observed. It may be, therefore, conceived that the polymerization reaction was performed in 100%. A number-average molecular weight was 29,700 and polydispersibility of the polymer obtained was 1.10, respectively.

IR(KBr): 1740, 1665 cm$^{-1}$ (>C=O)
$^1$H-NMR(270 MHz, DMSO-d$_6$):δ; 1.40(br, 3H) 2.01 (s, 5H), 7.00 (br, 2H), 7.53 (br, 2H), 9.89 (br, 1H)
IR and NMR data corresponded with those of polymeric compound obtained by solution polymerization using radical initiator.

Example 2

To dried dimethylformamide (DMF) (20 ml) were added potassium salt (0.58 g; 2.1 mmol) of theophylline acetate so as to suspend the latter, followed by slowly adding dropwise 1-chloro-2-methacryloyloxyethylene (0.4 g; 2.7 mmols) and heated at 100° C. for 5 hours. After the completion of the reaction, the solvent was removed by distillation. The residue was dissolved in chloroform (100 ml), followed by washing twice with water (20 ml). After removing the solvent by distillation, the recyrstallization from benzene was carried out.

The yield of the resulting methacryloyloxyethyltheophylline was 0.48 g.

The following are the data on crystalline form, melting point, elemental analysis, IR, $^1$NMR and UV spectrum.

Colorless plate crystal
Melting point: 125°–126° C.
Elemental analysis: $C_{15}H_{18}N_4O_6$ (350.33)

|  | C | H | N |
|---|---|---|---|
| Calculated | 51.43 | 5.18 | 15.99 |
| Found | 51.48 | 5.24 | 15.87 |

IR(KBr): 1745, 1710, 1695, 1660 cm$^{-1}$ (>C=O)
$^1$H-NMR(270 MHz, CDCl$_3$): δ; 1.9 (S, 3H, CH$_3$; vinyl group), 3.3–3.6 (d, 6H, CH$_3$: theophylline), 4.3–5.1 (m, 6H, —CH$_2$—), 5.5–6.0 (d, 2H, >C=CH$_2$), 7.5 (s, 1H, 8-H: theopylline)
UV(ethanol): $\lambda_{max}$; 244 nm(ε=13500), MS:m/e 350(M$^+$)

The resulting monomer (100 mg) were put into the grinder provided with a stainless steel mill under atmosphere of nitrogen and ground for 45 minutes to obtain a polymer.

When the polymer obtained was analyzed by means of $^1$H-NMR spectrum, the protons contained in the olefin constituting the monomer were completely absent and peaks of strength (broad) corresponding to alkyl site were observed. It may be therefore conceived that the polymerization reaction was performed in 100%.

IR(KBr): 1700, 1655 cm$^{-1}$ (>C=O)
$^1$H-NMR(270 MHz, CdCl$_3$): δ; 0.86–1.03 (br, 3H), 1.90 (br, 2H),3.30 (s, 3H), 4.19 (br, 2H), 4.40 (br, 2H) 5.17 (br, 2H), 7.70 (s, 3H),

IR and $^1$H-NMR spectra corresponded with those of polymeric compound obtained by solution polymerization using radical initiator.

Example 3

1-Methacryloyloxymethyl-5-fluorouracil was synthesized according to the process described in the Publication (SHOICHIRO OZAKI et al., Japanese Patent Application Laid-open No.61467/1989). The monomer (100 g) thus obtained were ground under atmosphere of nitrogen for 45 minutes by using a grinder provided with a stainless steel mill to obtain a polymer. When the polymer obtained was analyzed by means of $^1$H-NMR spectrum, the protons contained in olefin constituting the monomer were completely disappeared and peaks of strength (broad) corresponding to alkyl site were observed. It may be therefore conceived that the polymerization reaction was performed in 100%.

IR(KBr): 3450, 1700 cm$^{-1}$, $^1$H-NMR(DMSO-d$_6$): δ; 0.80–1.05(br, 3H), 1.90 (br, 2H), 5.58 (br, 2H), 8.11 (br, 1H), 12.00 (br, 1H)

IR and $^1$H-NMR spectra corresponded with those of polymer obtained by solution polymerization using radical initiator.

Example 4

25 Mg of acrylamide and 77 mg of p-methacryloyoxyacetanilide were ground under atmosphere of nitrogen for 45 minutes by using a grinder provided with a stainless steel mill. To the sample thus ground were added 20 ml of water and left to stand at a room temperature for one hour. The whole was centrifuged twice at 3000 rpm for 45 minutes. The resultant precipitate was dried under reduced pressure at 60° C. Then, 20 ml of a mixed solution of water and dimethylformamide in the ratio of the 1 to 1 were added. The whole was left to stand at a room temperature for one hour, followed by centrifuging twice at 3000 rpm for 15 minutes. The resultant supernatant liquid was removed by distillation. The precipitate was dried under a reduced pressure at 60° C. The yield of a random copolymer of p-methacryloyloxyacetanilide and acrylamide was 88.4 mg.

Example 5

50 Mg of polyacrylamide and 50 mg of 1-methacryloyl-5-fluorouracil were ground under atmosphere of nitrogen for 45 minutes by using a grinder provided with a stainless steel mill. To the sample thus ground were added 20 ml of acetone and left to stand at a room temperature for 30 minutes. The whole was then centrifuged twice at 3000 rpm for 15 minutes. The resultant supernatant liquid was removed. To the reminder was added 20 ml of acetone again and the whole was treated in the same manner. The residue was dried under reduced pressure. Then, 20 ml of water were added. The whole was left to stand at a room temperature for one hour, following by centrifuging twice at 3000 rpm for 15 minutes. After removal of the supernatant liquid by distillation, the resultant precipitate was dried under reduced pressure at 60° C. The yield of a block copolymer of 1-methacryloyl-5-fluorouracil and polyacrylamide was 18.8 mg.

1-Methacryloyl-5-fluorouracil was synthesized according to the process described in the publication (Mitsuru AKASHI et al., J. Bioact. Compat. Polym. 1987 2. pp.120–130).

[Effects of the Invention]

The following experiments are given, in order to confirm that the polymeric drug of this invention is a prodrug releasing a physiological active substance.

Experiment 1

Into an egg apple shaped flask of 30 ml were added 5 mg of the polymer obtained by Example 1 or 2, followed by adding 2 ml of DMF to dissolve the former. The whole was then dried under reduced pressure using rotary evaporator on a water bath heated at 80° C. to form a thin layer on the inner wall of the flask. 20 Ml of hydrolytic solution having the composition specified below were added into the flask and sampling was carried out at 37±0.2° C. with lapse of time to determine the quantity of the drug released.

Composition of hydrolytic solution:

dioxane: pH 8 0.05M phosphoric acid buffer solution=1:1

The quantity of the drug released was determined by 245 nm UV absorption of Example 1 and by 274 nm UV absorption of Example 2, respectively. The results obtained are shown in Table 1.

TABLE 1

| | Rate of hydrolysis (%) | |
|---|---|---|
| Time | Example 1 | Example 2 |
| 0 | 0 | 0 |
| 1 | 60 | 28 |
| 3 | 62 | 40 |
| 5 | 63 | 52 |
| 20 | 77 | 70 |
| 30 | — | 75 |
| 40 | 80 | — |
| 120 | 83 | 95 |

As shown in Table 1, it is clear that the polymeric drug of this invention can release drug in a solution.

Experiment 2

5 Mg of the polymer obtained by Example 2 were subjected to form a thin layer on the inner wall of the flask in the same manner as Experiment 1. And, the quantity of the drug released was determined similarly as in Experiment 1 by using a hydrolytic solution having the composition specified below. The results obtained are shown in Table 2.

Composition of hydrolytic solution:

ethanol: pH 8 0.05M phosphoric acid buffer solution=1:1

TABLE 2

| | Rate of hydrolysis (%) |
|---|---|
| Time | Example 1 |
| 7 | 5 |
| 20 | 18 |
| 30 | 33 |
| 45 | 52 |
| 50 | 57 |

As shown in Table 2, it is clear that the polymeric drug of this invention can also release drug in a mixing solution of ethanol and phosphoric acid buffer solution.

What is claimed is:

1. A process for the preparation of a random copolymer of acrylic acid or methacrylic acid derivatives having the formula:

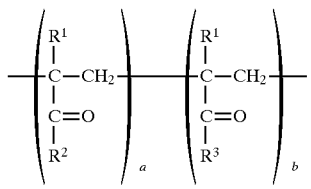

wherein $R^1$ represents a hydrogen atom or methyl group; $R^2$ represents a residue after bonding by ester linkage or amide linkage in a compound having physiological activity which is bonded with a carboxyl group by ester linkage or amide linkage; $R^3$ represents a hydroxyl group, methoxyl group or amino group; a is an integer ranging from 20 to 1,500; and b is an integer ranging from 1 to 100, which comprises polymerizing a compound having the formula:

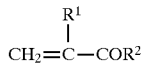

wherein $R^1$ and $R^2$ have the same meanings as defined above, with a compound having the formula:

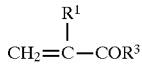

wherein $R^1$ represents a hydrogen atom or methyl group and $R^3$ represents a hydroxyl group, methoxyl group or amino group, the latter compound being selected from the group consisting of acrylic acid, methacrylic acid, acrylamide and methacrylamide, in solid phase in the absence of solvent under mechanical force.

2. The process described in claim 1, wherein the polymerization reaction is a mechanochemical polymerization reaction of compounds that can form an anion radical by electron transfer from an activated metal surface.

3. The process described in claim 1, wherein the polymerization reaction is a mechanochemical polymerization reaction of compounds that can form an anion radical by electron transfer from an activated metal surface, conducted under reduced pressure or an atmosphere of nitrogen, by a mechanical energy of grinding, rubbing, high-speed vibration or compression.

* * * * *